US009168555B2

(12) United States Patent
Tsai et al.

(10) Patent No.: US 9,168,555 B2
(45) Date of Patent: Oct. 27, 2015

(54) METHOD FOR TRANSPORTING A LIQUID FOR ATOMIZATION AND A METHOD AND DEVICES FOR ATOMIZING THE SAME

(71) Applicants: Chen S. Tsai, Irvine, CA (US); Shirley C. Tsai, Irvine, CA (US)

(72) Inventors: Chen S. Tsai, Irvine, CA (US); Shirley C. Tsai, Irvine, CA (US)

( * ) Notice: Subject to any disclaimer, the term of this patent is extended or adjusted under 35 U.S.C. 154(b) by 356 days.

(21) Appl. No.: 13/764,353

(22) Filed: Feb. 11, 2013

(65) Prior Publication Data

US 2013/0146677 A1 Jun. 13, 2013

Related U.S. Application Data

(62) Division of application No. 12/788,212, filed on May 26, 2010, now Pat. No. 8,434,473.

(60) Provisional application No. 61/220,964, filed on Jun. 26, 2009.

(51) Int. Cl.

| | |
|---|---|
| ***A61M 11/00*** | (2006.01) |
| ***B05B 17/06*** | (2006.01) |
| *A61M 15/00* | (2006.01) |

(52) U.S. Cl.

CPC ......... *B05B 17/0623* (2013.01); *B05B 17/0669* (2013.01); *A61M 11/005* (2013.01); *A61M 15/0085* (2013.01)

(58) Field of Classification Search

CPC ............ A61M 15/0085; A61M 11/005; B05B 17/0623; B05B 17/0669

USPC ................ 128/200.16; 239/102.1, 102.2, 101

See application file for complete search history.

(56) References Cited

U.S. PATENT DOCUMENTS

| | | | | |
|---|---|---|---|---|
| 4,474,326 | A * | 10/1984 | Takahashi | 239/102.2 |
| 6,467,331 | B1 * | 10/2002 | Kline-Schoder et al. | 73/19.03 |
| 8,143,318 | B2 * | 3/2012 | Wenzel et al. | 516/21 |
| 8,434,473 | B2 * | 5/2013 | Tsai et al. | 128/200.16 |
| 2003/0048038 | A1 * | 3/2003 | Tsai | 310/328 |
| 2009/0014551 | A1 * | 1/2009 | Babaev | 239/102.2 |

* cited by examiner

*Primary Examiner* — Steven Douglas

(74) *Attorney, Agent, or Firm* — Marcus C. Dawes; Daniel L. Dawes

(57) ABSTRACT

Ultrasonic nozzle devices without a central channel but employing a design of cascaded multiple Fourier horns in resonance produce micrometer-sized monodisperse or narrowly-sized droplets with greatly reduced electrical drive power requirements. The liquid to be atomized is brought externally to or adjacent to the endface of the nozzle tip. The above liquid transport method is equally applicable to the ultrasonic nozzle-array devices that are made up of a plurality of ultrasonic single-nozzle devices configured in parallel. The longitudinal length, transverse width, shape, and area of the nozzle endface of single-nozzle and nozzle-array devices may be tailored or designed (e.g. enlarged) to obtain optimum or large quantities of product droplets to achieve high throughput. By increasing the drive frequency to 8 MHz or higher, sub-micrometer-sized monodisperse or narrowly-sized droplets can be produced using the ultrasonic single-nozzle and nozzle-array devices or any solid endface.

9 Claims, 4 Drawing Sheets

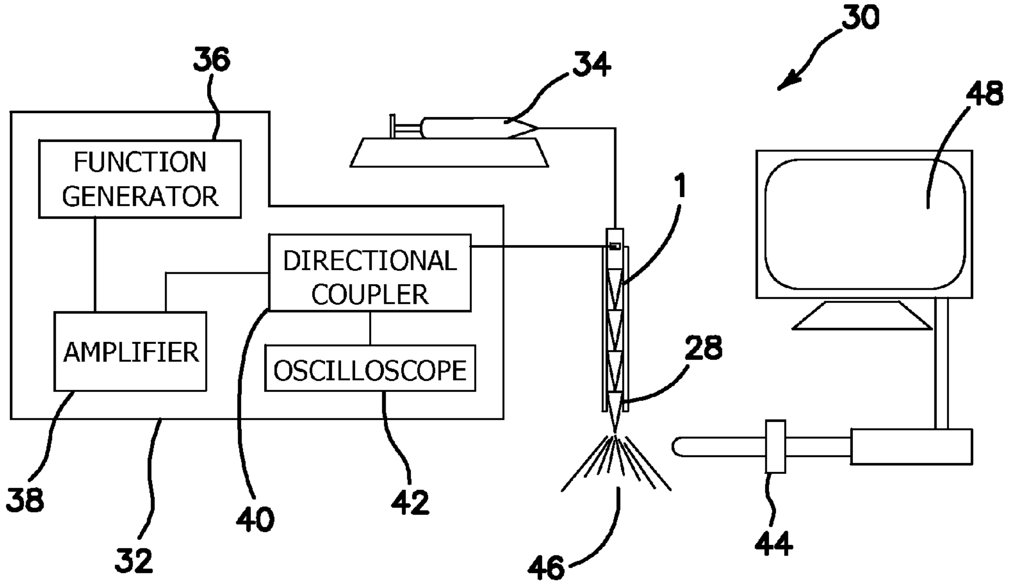
FIG. 3
FIG. 5
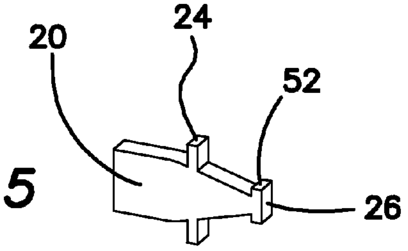
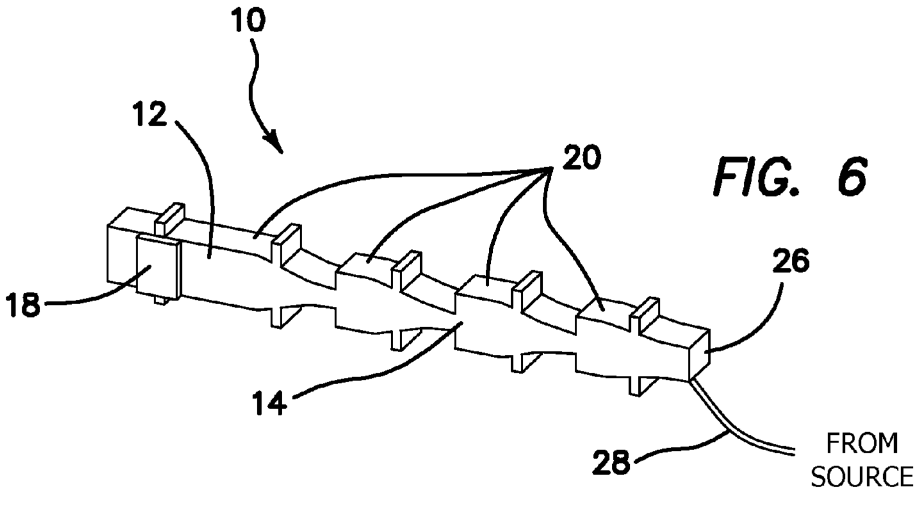
FIG. 6

METHOD FOR TRANSPORTING A LIQUID FOR ATOMIZATION AND A METHOD AND DEVICES FOR ATOMIZING THE SAME

RELATED APPLICATIONS

The present application is a divisional of U.S. application Ser. No. 12/788,212, filed on May 26, 2010, now U.S. Pat. No. 8,434,473, which is incorporated herein by reference and to which priority is claimed pursuant to 35 USC 120. The present application is related to U.S. Provisional Patent Application, Ser. No. 61/220,964 filed on Jun. 26, 2009, which is incorporated herein by reference and to which priority is claimed pursuant to 35 USC 120.

STATEMENT OF GOVERNMENT SUPPORT

This invention was made with government support under grant 5R21 EB006366 awarded by the National Institute of Health. The government has certain rights in the invention

BACKGROUND OF THE INVENTION

1. Field of the Invention

The invention relates to the field of production of micrometer- and sub-micrometer-sized monodisperse or narrowly-sized droplets and transport of the liquid feed. Monodisperse or narrowly-sized droplets less than 10 μm in diameter in sprays are highly desirable in nanoparticles synthesis from heat sensitive precursor solutions because they can be processed at a conveniently low temperature and atmospheric pressure. Also, monodisperse or narrowly-sized droplets (particles) 1 to 6 μm in diameter have multiple biomedical applications including pulmonary drug delivery, micro encapsulation of drugs, and drug preparation for inhalation. Other potential applications include thin-film coating and three-dimensional (3-D) spray coating for micro- and nano-electronics and photonics.

2. Description of the Prior Art

Droplet (or drop) formation based on acoustic techniques has been an important research and development subject area in recent years because of its various potential applications. For example, nozzle-less droplet ejectors that use focused acoustic waves at 5-900 megahertz (MHz) to eject micrometer-sized droplets, one drop at a time, are applicable to high-resolution ink-jet printing. A micromachined ultrasonic droplet generator based on a liquid horn structure is capable of droplet ejection from 5- to 10-μm orifices at multiple resonant frequencies between 1 and 5 MHz and has been shown to be applicable to inhalation drug therapy. Piezoelectrically actuated flextensional micromachined ultrasonic transducers with annular piezoelectric disk and operating resonance frequencies from 450 kHz to 4.5 MHz have also been designed and fabricated for droplet ejection. Current ultrasonic nebulizers that use vibrating micrometer-sized mesh technology are also capable of producing micrometer-sized droplets for applications such as pulmonary drug delivery, but the resulting drop size distributions are rather broad because various atomization mechanisms such as cavitation, impinging, and jetting are also involved in addition to the capillary wave mechanism. Furthermore, the electrical drive power required is typically greater than 10 W. Finally, commercially available metal-based bulk-type ultrasonic nozzles (Sono-Tek Corp., Milton, N.Y.) that use capillary waves at frequencies far below 1 MHz are capable of producing sprays of droplets (mist) with a diameter smaller than the nozzle orifice diameter, but much larger than 10 μm. All of the aforementioned devices under research and development and commercial devices are either incapable of producing monodisperse or narrowly-sized droplets of such desirable size range (1 to 6 μm) or producing them only at very low throughput. Furthermore, they are bulky, requiring much higher electrical drive power, and do not have potential for mass production using batch fabrication. Clearly, it is desirable to explore and realize miniaturized ultrasonic nozzle devices that operate at megahertz drive frequencies for producing sprays of micrometer-sized or even sub-micrometer-sized droplets with narrow size distributions, or even monodisperse droplets, at high throughput and low electrical drive power.

Additionally, several attempts have been made in the prior art to transport the liquid to be atomized through the ultrasonic nozzle in which it is to be ejected from. Typically, a central channel was used in the prior art to transport the liquid to be atomized to the endface of the nozzle tip of the single-nozzle ultrasonic device. Specifically, in the Sono-Tek metal-based bulk-type ultrasonic nozzle referred to earlier a cylindrical channel is bored through the nozzle body. In the silicon-based multiple Fourier horns ultrasonic device a pair of identical nozzles each with an etched trough along the nozzle axis was bonded to form a 200 μm×200 μm central channel for transport of the liquid to the endface of the vibrating nozzle tip. As the amplitude of vibration on the endface of the nozzle tip in the direction perpendicular or nearly perpendicular to the endface reaches a threshold or critical vibration amplitude at the MHz resonance frequency of the multiple Fourier horns, the liquid resting on the endface is broken into micrometer-sized monodisperse or narrowly-sized droplets. Formation of this central channel requires several additional micro-fabrication steps. Furthermore, as the operating frequency of the nozzle increases, the physical size of the device decreases. As a result, the area of the vibrating endface decreases, and the degree of complexity involved in channel fabrication increases. Finally, the corresponding reduction in the channel cross section will result in decreased liquid flow rate and, thus, droplet throughput.

What is needed is a method and device or devices that eliminate the need for a central channel and its corresponding fabrication complexities while at the same time maintaining a high flow rate and a high-throughput production of monodisperse or narrowly-sized droplets in micrometer and sub-micrometer sizes, and low electrical drive power.

BRIEF SUMMARY OF THE INVENTION

The miniaturized silicon-based megahertz (MHz) ultrasonic nozzle devices presented herein solve these problems and more by employing a design of multiple Fourier horns in resonance which activates a pure capillary wave atomization mechanism and produce monodisperse or narrowly-sized micrometer- and sub-micrometer-sized droplets with greatly reduced electrical drive power requirements.

Silicon-based ultrasonic nozzles have several advantages over conventional metal-based bulk-type ultrasonic nozzles found in the prior art. Silicon possesses a relatively large electromechanical coupling coefficient. More importantly, mass production of any similar or different nozzle profiles can be readily accomplished using the well-established inductive coupled plasma (ICP) process of microelectromechanical system (MEMS)-based fabrication technology.

We have recently established that the underlying physical mechanism for atomization or droplets generation, namely, temporal instability of Faraday waves (also called standing capillary waves) is related to the "critical vibration amplitude" in the direction perpendicular or nearly perpendicular to the endface of the nozzle tip to form a layer of liquid on the endface, but is not related to the means of liquid transport to the endface of the nozzle tip or the device configuration or method used for excitation of the critical vibration amplitude. As a result of the above basic concept, the central channel of the prior art may be replaced by simple means of externally bringing the liquid to the endface of the nozzle tip. For example, tubing such as fused silica, Teflon®, metal, or a light wicker connected to the source of liquid at one end and in touch with or close to the endface of the nozzle tip at its opposing end will serve the purpose. Thus, it must be understood that "tubing" within this specification and its claims shall mean any means, mechanism, micropiping, channel, conduit or device for transporting liquid, nanoparticles dispersion, or other material to be atomized from a source of the same to or near the nozzle endface. The above basic concept further suggests that device configurations such as a single nozzle alone without a central channel and a simple solid endface vibrating with corresponding "critical amplitude" at a given drive frequency may be used to produce monodisperse or narrowly-sized droplets. It should also be noted that the resonance effect among the multiple Fourier horns of a single-nozzle device readily generates the required "critical vibration amplitude" for atomization of the liquid resting on the endface of the nozzle tip at a low electrical drive power.

Accordingly, elimination of the central channel greatly simplifies the MEMS-based micro fabrication steps for the single-nozzle devices and thus, reduces their ultimate manufacturing costs. The above liquid transport method is equally applicable to the ultrasonic nozzle-array devices that are comprised of a plurality of ultrasonic single-nozzle devices configured in parallel.

The longitudinal length, transverse width, shape, and area of the nozzle endface of single-nozzle and nozzle-array devices may be tailored or designed (e.g. enlarged) to obtain optimum or large quantities of product droplets to achieve high throughput. Replacement of the central channel with judicious design of the endface or end plate of the nozzle tip in length, width, shape, and area facilitates direct transport of a large quantity of the liquid to the endface and, thus, achieves high-throughput of product droplets for many applications such as inhalation or pulmonary drug delivery, micro encapsulation of drugs, thin-film coating, three-dimensional (3-D) spray coating for micro- and nano-electronics and -photonics, and nanoparticles synthesis. It is to be expressly understood that the liquid referred to in the current invention includes pure-substance liquid, solution, and nanoparticles dispersion.

The method of the illustrated embodiments are applicable to any vibrating solid surface provided that its vibration amplitude (displacement) in the direction perpendicular or nearly perpendicular to the surface reaches the corresponding "critical amplitude" or higher for a given drive frequency of vibration. Since the droplet diameter is inversely proportional to the drive frequency to the ⅔ power, by increasing the drive frequency to 8 MHz or higher, sub-micrometer-sized monodisperse or narrowly-sized droplets may be produced.

Such an advantage is applicable to the ultrasonic devices which utilize an array of single-nozzle device configured in parallel. The method for liquid transport facilitates high-throughput production of micrometer- and sub-micrometer-sized monodisperse or narrowly sized droplets for inhalation or pulmonary drug delivery. Current devices (e.g., nebulizers, metered dose and dry powder inhalers) all suffer from broad droplet or particle size distributions and low throughput, which make it difficult to deliver sufficient drug to targeted sites precisely and rapidly. In intubated patients, polydisperse aerosols also limit delivery through the ventilator tubing for adults and especially in neonates. Thus, there is a need for a droplet (aerosol) device that produces more uniform or even monodisperse droplets or aerosols with increased throughput of drug delivery to reduce treatment time, small physical size for easy access to target, and low electrical drive power. The illustrated embodiments of the invention facilitate realization of a miniaturized ultrasonic high-throughput micron- and submicron-sized monodisperse droplet device to fulfill such an unmet need. Therefore in one particular embodiment, the device of the current invention may be battery powered and pocket sized in order to function as a miniaturized monodisperse medicinal nebulizer for popular and outpatient use.

While the device and method has been or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 3 is a schematic diagram of an atomization apparatus employing the silicon single-nozzle device seen in FIG. 1.

FIG. 5 is a magnified perspective view of the enlarged or hammer head nozzle tip or endface seen within the nozzle-array device of FIG. 2.

FIG. 6 is a perspective view of a silicon-nozzle device with four Fourier horns, the most distal Fourier horn comprising an enlarged or hammer head nozzle tip or endface.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
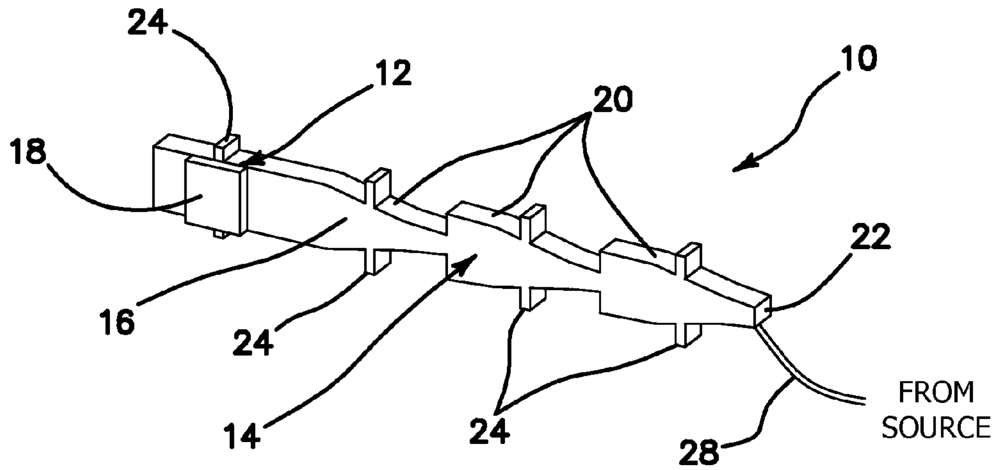
FIG. 1 is a perspective view of a silicon single-nozzle device consisting of a drive section and a resonator section with three Fourier horns, the most distal Fourier horn comprising a normal nozzle tip or endface.

The miniaturized ultrasonic nozzle device 1 of the current invention is comprised of a silicon single-nozzle device, generally denoted with reference numeral 10 as seen in FIG. 1, supported by two silicon strips, one on each side (not shown) and coupled to the nodal bars 24 that are disposed laterally through the silicon single-nozzle device 10. It is to be expressly understood that the single-nozzle device 10 in FIG. 1 is equivalent to the miniaturized ultrasonic nozzle device 1, and is used henceforth for brevity. The single-nozzle device 10 comprises a drive section 12 and a resonator section 14 in a common silicon substrate 16 that is made of one or more pieces of silicon wafers. The drive section 12 comprises a piezoelectric transducer such as lead zirconate titanate (PZT) 18 coupled to the rectangular shaped base of the silicon substrate 16 using a silver paste as is known in the art. It is to be expressly understood, however, that other forms of bonding such as welds, alloys, or other pastes or resins now known or later devised may also be used without departing from the original spirit and scope of the invention.

In one embodiment, the resonator section 14 of each silicon single-nozzle device 10 comprises three Fourier horns 20. Each Fourier horn 20 is half a wavelength long with a longitudinal vibration amplitude (displacement) magnification of two. Other magnifications smaller than two may also be used without departing from the spirit and scope of the invention. The drive section 12 and each Fourier horn 20 also comprise a nodal bar 24 that is disposed laterally through the silicon single-nozzle device 10. The most distal Fourier horn 20 in the resonator section 14 comprises a normal nozzle tip or endface 22.

Excitation of the PZT transducer plates 18 by an AC voltage at the nozzle resonant frequency creates a standing acoustic wave along the single-nozzle device 10 with a maximum longitudinal vibration (displacement) at the nozzle tip or endface 22 of the silicon single-nozzle device 10. The resonance effect of the multiple Fourier horns 20 greatly enhances the longitudinal displacement on the nozzle endface 22. As a result of the vibration, Faraday waves are formed on the free surface of the liquid layer resting on the nozzle tip or endface 22. Subsequent breakup of the Faraday waves results in atomization and production of monodisperse or narrowly-sized droplets.

The silicon ultrasonic single-nozzle device 10 is preferably fabricated using MEMS technology. The ultrasonic single-nozzle device 10 is fabricated according to the desired resonant frequency to be used, the dimensions of the single-nozzle device 10 being larger for when a relatively low resonant frequency is to be used, and smaller dimensions for when a higher resonant frequency is to be used. For example, in order to have a relatively low resonant frequency of 0.5 MHz the dimensions of the single-nozzle device 10 may be 3.66 cm×0.38 cm×0.11 cm while for a higher resonant frequency of 1.5 MHz, the dimensions of the single-nozzle device 10 may be 1.20 cm×0.15 cm×0.05 cm. These dimensions of the single-nozzle device 10 are meant to be illustrative purposes only. Other substantially similar dimensions for the single-nozzle device 10 may also be used in order to obtain substantially similar resonant frequencies without departing from the original spirit and scope of the invention.

Liquid from an outside source (not seen) flows through a tubing 28 and issues onto the nozzle tip or endface 22 which vibrates longitudinally at the nozzle resonance frequency. The tubing 28 may be comprised of metal or metal alloys, plastic or plastic composites, or a light wicker with its distal end in contact with or in close proximity to the endface of the nozzle tip 22. When the vibration amplitude of the nozzle endface 22 exceeds a threshold (critical amplitude), a liquid layer is maintained on the nozzle endface 22 and the Faraday waves, formed on the free surface of the liquid layer, grow exponentially in amplitude, resulting in generation of droplets.

Atomization of the liquid is carried out at room temperature (20° C.) using, for example, deionized (DI) water, 0.25% nonionic surfactant (Triton X-100) solution, ethanol (ethyl alcohol), aqueous glycerol solution, aqueous and ethanol solutions of isoproterenol (salbutamol or albuterol), insulin, and aqueous gold nanoparticles dispersion. Because the single-nozzle device 10 takes advantage of the resonance effect, the electric drive power required for atomization is too low to cause any significant increase in temperature. In fact, the temperature in the drive section 12 at an electrode voltage even higher than that required for atomization was measured to increase by less than 2° C., and no change in the temperature of the atomization liquids, was detected by a thermocouple.

When the ultrasonic single-nozzle device 10 shown in FIG. 1 is driven at its resonant frequency of 971.1 kHz by the drive system 32 and PZT transducer 18, each of the three Fourier horns 20 in cascade in each ultrasonic single-nozzle device 10 vibrates longitudinally with neither flexural nor lateral motion. Furthermore, the maximum magnitude of longitudinal vibration or displacement at each succeeding Fourier horn 20 tip increases progressively by a factor of 2, resulting in an overall vibration displacement magnification of 8 (theoretical design $2^3=8$) on the nozzle tip or endface 22.

Figure 4:
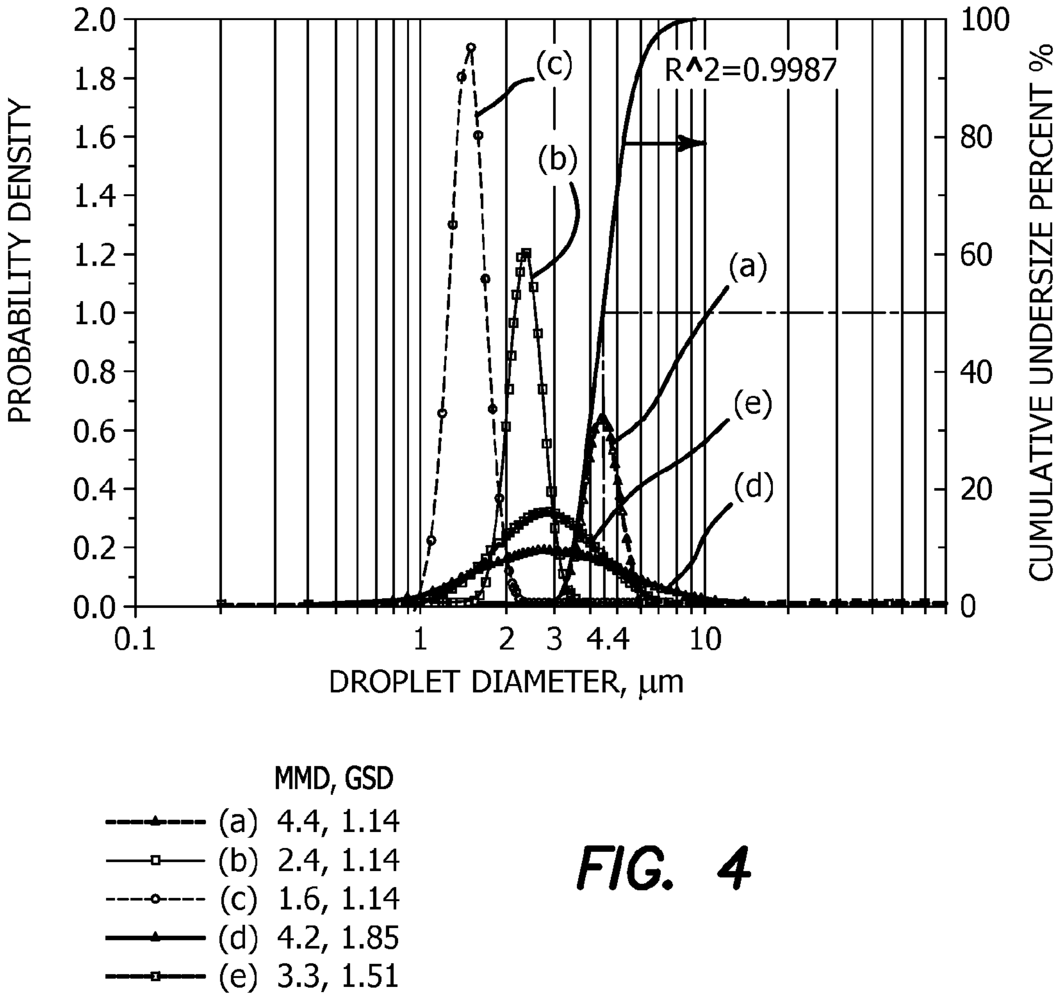
FIG. 4 is a graph of size distribution in terms of probability density and cumulative undersize percentage versus droplet diameter for water (plot (a) at 1.0 MHz) and alcohol droplets (plot (b) at 2.0 MHz and plot (c) at 2.5 MHz) produced by the silicon single-nozzle device seen in FIG. 1 and the size distributions of droplets produced by two commercial nebulizers (plots (d) and (e)).

The sizes and size distributions of the droplets produced by the ultrasonic single-nozzle device 10 are measured using laser light diffraction technique provided by the Malvern/Spraytec System (Model #STP5311). The measured results for the water droplets produced by a 1.0 MHz and for the alcohol droplets produced by a 2.0 MHz and a 2.5 MHz single-nozzle device 10 are shown in FIG. 4. The droplets are clearly monodisperse with geometrical standard deviation (GSD) as small as 1.14 and respective MMD of 4.4 μm, 2.4 μm, and 1.6 μm. Note that GSD of 1.0 corresponds to single size and GSD up to 1.22 is commonly accepted as monodisperse in aerosol medicine. MMD is a measure of droplet size and stands for mass median diameter. In addition, the measured electrical drive power was found as low as 55 -160 mW at the droplet throughput of 0.42 to 0.65 ml/min. The low drive power requirement made possible by the concept of multiple Fourier horns 20 in resonance is supported by the theoretical calculation described in further detail below.

The atomization and production of micrometer-sized monodisperse or narrowly-sized droplets by the ultrasonic single-nozzle device 10 is made possible by the temporal instability of Faraday waves, also called standing capillary waves. Faraday waves are generated on the free surface of the liquid resting on the planar or nearly planar endface of the nozzle tip when the peak longitudinal excitation displacement (h) of the endface (at the drive frequency f) reaches a critical value $h_{cr}$. The amplitude ξ(x,t) of the resulting Faraday waves with initial amplitude $\xi_o$ is given by the following equation:

$$\xi(x,t)=\xi_o\, e^{\pi k f (h-h_{cr}) t}\sin(2\pi(f/2)t-\pi/4)\cos kx \qquad (1)$$

In which t designates time and k=2π/λ is the wave number of the Faraday waves, and the X-axis is perpendicular to the nozzle axis and parallel to the width of nozzle endface. The frequency of the Faraday waves is seen as equal to one half of the drive frequency, and the corresponding Faraday wavelength λ is determined by the Kelvin equation:

$$\lambda=(8\pi\sigma/\rho)^{1/3}f^{-2/3} \quad (2)$$

in which f, σ, and ρ are the ultrasonic drive frequency, the surface tension, and the density of the liquid, respectively. Clearly, the Faraday waves generated become temporally unstable when the peak excitation displacement h exceeds the critical value $h_{cr}$ for Faraday wave formation given as follows:

$$h_{cr}=2\nu\{\rho/(\pi f\sigma)\}^{1/3} \quad (3)$$

where the liquid kinematic viscosity $\nu=\mu/\rho$ in which μ is the liquid viscosity. The amplitude of the Faraday waves at MHz drive frequency grows rapidly once the excitation displacement h exceeds the critical value $h_{cr}$, and the Faraday waves become unstable, resulting in atomization and production of monodisperse or narrowly-sized droplets.

Finally, the diameter ($D_p$) of the droplets produced is proportional to the Faraday wavelength as given in Equation 4:

$$D_p=C\lambda \quad (4)$$

where the proportionality constant C ranges from 0.34 to 0.40.

Close agreement between the predicted and the measured diameters of the droplets produced by the ultrasonic nozzle devices with a single-nozzle device 10 operating at 0.5, 1.0, 1.5, and 2.0 MHz is shown in Table 1 below. The narrow bandwidth of the atomization frequency made possible by the novel design of multiple Fourier horns 20 in resonance results in production of monodisperse droplets with GSD as low as 1.1.

TABLE 1

Measured droplet diameters are in agreement with predicted values of $D_p$ = 0.40λ.

| Drive freq. f (MHz) (Nominal) | Liquid | Surface Tension σ (dyn/cm) | Density ρ (g/cm³) | Faraday Wavelength λ[a)] (μm) | Droplet dia. $D_p$ (μm) Pred'd 0.40λ | Meas'd [b)] |
|---|---|---|---|---|---|---|
| 0.5 | Water | 72 | 1.00 | 19.6 | 7.83 | 7.11 |
| 1.0 | Water | 72 | 1.00 | 12.2 | 4.88 | 4.64 |
| 1.0 | Glyc. aq[c)] | 72 | 1.11 | 11.7 | 4.71 | 4.51 |
| 1.0 | Alcohol | 23 | 0.79 | 9.0 | 3.60 | 3.47 |
| 1.5 | Water | 72 | 1.00 | 9.3 | 3.72 | 3.66 |
| 1.5 | Glyc. aq[c)] | 72 | 1.10 | 9.0 | 3.59 | 3.73 |
| 1.5 | Alcohol | 23 | 0.79 | 6.9 | 2.76 | 2.49 |
| 2.0 | Water | 72 | 1.00 | 7.7 | 3.08 | 2.89 |
| 2.0 | Alcohol | 23 | 0.79 | 5.7 | 2.27 | 2.24 |

[a)]Faraday wavelength $\lambda = (8\pi\sigma/\rho)^{1/3} f^{-2/3}$,

[b)] Experimental errors: ±0.04 for 0.5, 1.0 and 1.5 MHz; ±0.08 for 2.0 MHz nozzles,

[c)]Aqueous solution of 40-44 wt % glycerol with viscosity up to 4.5 cP.

The temporal instability of Faraday waves also supports the very low electrical drive power the single-nozzle devices require for atomization. The critical vibration displacement $h_{cr}$ of 0.33, 0.29 and 0.26 μm predicted by Equation 3 for water at 1.0, 1.5, and 2.0 MHz drive frequencies, respectively, are to be compared to the measured peak excitation displacements of 0.34, 0.32, and 0.31 μm required for atomization using a laser Doppler vibrometer (Polytech GmbH, Model PSV 400). The fact that the measured peak excitation displacements are only slightly higher than the predicted $h_{cr}$ values verifies that the MHz Faraday waves rapidly become unstable and result in atomization once the excitation displacement exceeds the critical vibration displacement. Thus, the low peak excitation displacements required for atomization support the low electrical drive power measured for atomization, namely, 55 to 160 mW at throughput of 0.35 to 0.65 ml/min with the 2.0, 1.5, and 1.0 MHz nozzles. Note that this range of drive power is at least two orders of magnitude lower than that required in conventional ultrasonic atomization using MHz disk transducers. This very low drive power requirement is attributable to the resonance effect of the three Fourier horns 20 used in the nozzles 10, since only a minute amount of power is needed to excite a nearly loss-free resonant system. The major sources of power losses that must be furnished by the electrical generator are the vibration of the nozzle endface, the lossy PZT transducer 18, the bonding between the PZT transducer 18 and the silicon substrate 16 in the drive section 12, and that between the pair of basic nozzles 10 required in the formation of a central channel in the case of earlier nozzles. The single-nozzle 10 and nozzle-array devices 50 without a central channel also have the advantage of lower electrical drive power for atomization.

In another embodiment, shown in FIG. 6, the single-nozzle device 10 comprises four Fourier horns 20 within the resonator section 14. The most distal Fourier horn 20 is designed with a longitudinal displacement magnification M ranging from 1.0 to 1.9, and comprises an enlarged nozzle tip or endface 26 in width that is larger than the normal nozzle tip 22. The addition of a fourth Fourier horn 20 increases the maximum magnitude of longitudinal displacement of the enlarged nozzle endface 26 by an additional magnification factor M, resulting in an overall vibration amplitude or displacement magnification or gain of 8M. The four Fourier horns 20 with enlarged nozzle endface 26 combine to significantly raise the throughput of the monodisperse or narrowly-sized droplets which may be produced by the single-nozzle device 10. It should also be understood that fewer or additional Fourier horns 20 other than what is shown in FIG. 6 may also be used without departing from the original scope of the invention.

Figure 2:
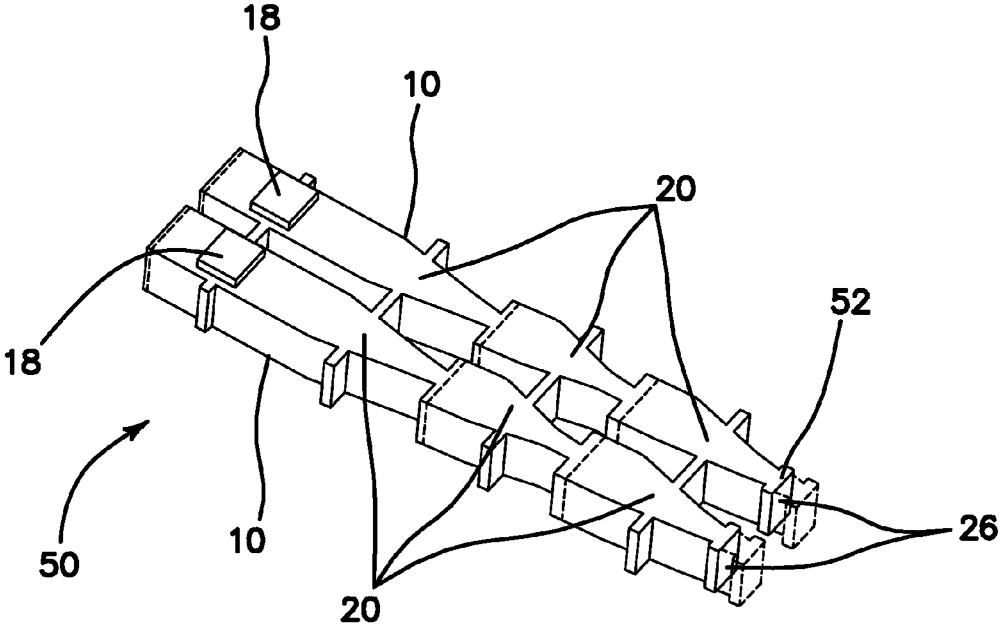
FIG. 2 is a perspective view of two silicon single-nozzle devices seen in FIG. 1 combined together in a nozzle-array device, wherein each of the single-nozzle devices comprises an enlarged or "hammer head" nozzle tip or endface.

In an alternative embodiment shown in FIG. 2, two identical silicon single-nozzle devices 10 are coupled in parallel to form an ultrasonic nozzle-array device 50. The drive sections 12 and resonator sections 14 of each single-nozzle device 10 are aligned and coupled side by side with the nodal bars 24 of each single-nozzle device 10 touching the nodal bars 24 of the adjacent single-nozzle device 10 as seen in FIG. 2. The distal Fourier horn 20 of each of the single-nozzle devices 10 of the current embodiment, however, comprises an enlarged or "hammer head" nozzle tip or endface 26 as seen in the magnified view of FIG. 5. The enlarged or hammer head nozzle endface or tip 26 comprises a wider width compared to that of the normal nozzle endface 22 and, therefore, may accommodate a higher droplet throughput than that of the nozzle tip 22.

It should be stressed that based on the theory of temporal instability of Faraday waves summarized above, formation of a liquid layer on the vibrating endface is essential for stable atomization to take place. However, formation of liquid layer is independent of how liquid is transported to the vibrating nozzle endface 22, 26. Therefore, other means of transporting a liquid other than by tubing 28 may also be used without departing from the original spirit and scope of the invention.

One such means is an end plate 52 which is coupled to the distal end of the Fourier horn 20 to form the hammer head nozzle tip or endface 26 of each individual silicon single-nozzle device 10 in the twin nozzle-array device 50 depicted in FIG. 2. The end plate 52 vibrates in unison with each corresponding single-nozzle device 10 in the direction perpendicular or nearly perpendicular to the surface of the end plate 52 along the nozzle axis as seen in the broken line outline in FIG. 2. Since the liquid to be atomized can be transported directly to the surface of the end plate 52, no central channel for liquid flow is needed. As liquid is fed onto the surface of the end plate 52, a liquid layer will be formed on it and stable atomization will take place when the vibration amplitude on the surface of the end plate exceeds the critical value given by Equation 3 above. Since the area of the vibrating hammer head or enlarged nozzle tip 26 comprising end plate 52 in contact with the liquid to be atomized is significantly larger than the usual tip area of just a nozzle tip alone 22, the nozzle-array device 50 will provide a much higher throughput of monodisperse or narrowly-sized droplets. The excellent agreement between the experimental results and the theoretically predicted values based on the theory of temporal instability of Faraday waves summarized above provides the solid scientific basis for such a new and novel nozzle-array configuration and the resulting devices. In accordance with Equation 4 above, the nozzle-array device 50 will produce 1.0 and 0.9 μm water droplets and alcohol droplets, respectively, at the operating frequency of 8 MHz. In one embodiment, each individual enlarged end plate 52 comprises the capability for simultaneous or sequential atomization of different liquids and their subsequent mixing desirable for some applications such as drug delivery to a patient. It should also be expressly understood that the number of single-nozzle device 10 in the nozzle-array device 50 can be readily increased via batch fabrication as commonly known in the art without departing from the original spirit and scope of the invention.

Figure 7:
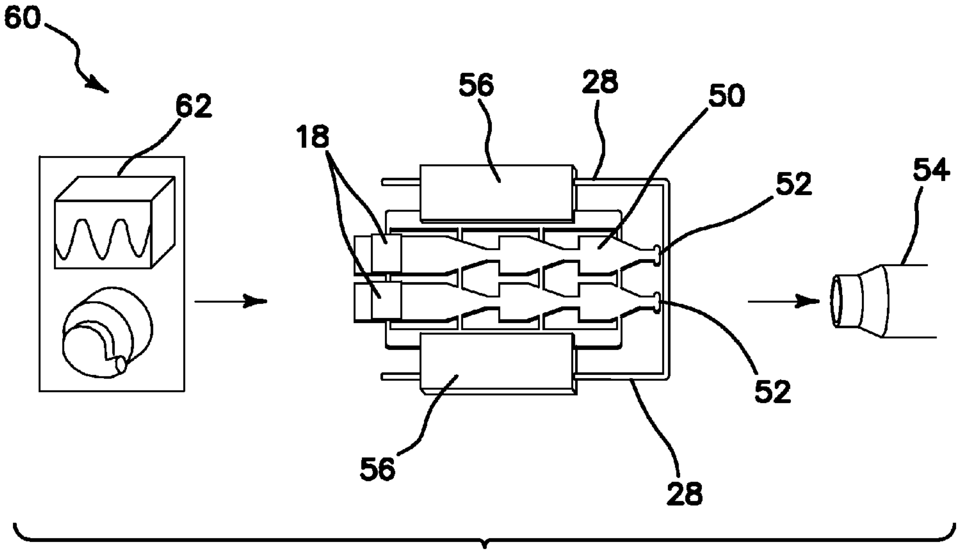
FIG. 7 is a schematic diagram of the platform for a miniaturized ultrasonic droplet generator employing the ultrasonic nozzle-array device seen in FIG. 2.

The implementation of the nozzle-array device 50 into a miniaturized ultrasonic droplet generator 60 can be seen in FIG. 7. The miniaturized ultrasonic droplet generator 60 comprises a driver module 62 coupled to the PZT transducers 18 of the nozzle-array device 50, wherein the driver module 62 comprises a function generator and amplifier on a small printed circuit board. The driver module 62 also comprises means for accurate setting and tuning of the drive frequency, control of the output power, and continuous or burst-mode of operation of the miniaturized droplet generator 60. The driver module 62 is small enough so that it may function as a convenient plug-in or battery powered unit as is known in the art.

The miniaturized ultrasonic droplet generator 60 also comprises a platform 56 which supports the nozzle-array device 50 and a plurality of tubing 28 which delivers the liquid to be atomized to the end plates 52 of the nozzle-array device 50. The platform 56 is coupled to the driver module 62 at its proximal end and to a mouth piece 54 at its distal end as depicted in FIG. 7. The mouth piece 54 has the general shape of a funnel and is used to direct the atomized liquid produced by the nozzle-array device 50 into the mouth and in turn the respiration system, for example, of a patient. Because of the low power demands of the nozzle-array device 50, the entirety of the miniaturized ultrasonic droplet generator 60 is small enough to be hand held or even pocket-sized and is powered by conventional batteries as is known in the art, In addition to each hammer head or enlarged nozzle tip 26 comprising its own end plate 52, in a separate embodiment, a single or common end plate (not shown) may also be coupled to some or all single-nozzle devices 10 contemporaneously within the nozzle-array device 50 and thus further increase the throughput of the monodisperse or narrowly-sized droplets.

Figure 8:
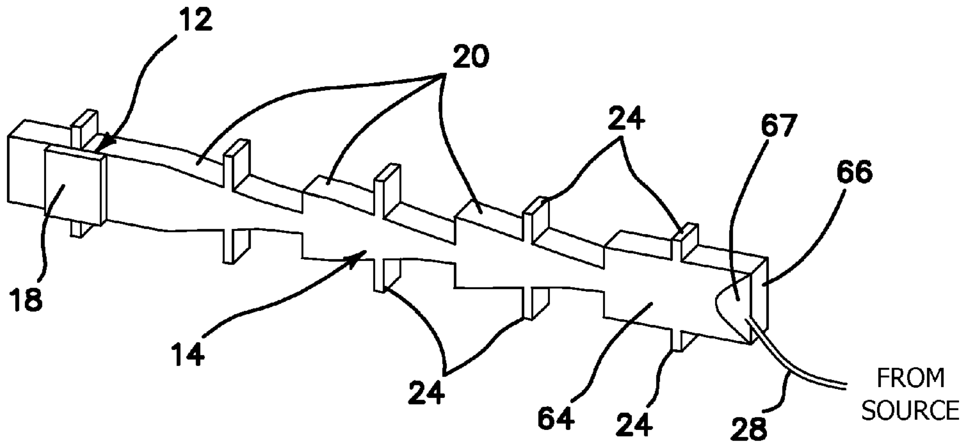
FIG. 8 is a perspective view of an alternative embodiment of the single-nozzle device seen in FIG. 1 with the most distal Fourier horn having longitudinal displacement magnification of one and, thus, a rectangular shaped end piece with an entrenched area for liquid feeding and large endface.

In still a further embodiment, the normal nozzle tip 22 of the single-nozzle device 10 seen in FIG. 1 may be enhanced by coupling an enlarged end piece 64 to the distal Fourier horn 20 as seen in FIG. 8. The end piece 64 comprising a trenched area 67 proximal to its large rectangular shaped nozzle endface 66 and vibrating in resonance with Fourier horns 20 is coupled to the distal Fourier horn 20 by means known in the art and comprises a nodal bar 24 disposed across its width so that it may be paired with at least one other single-nozzle device 10 in a nozzle-array device 50 similar to what is seen in FIG. 2. Liquid to be atomized is delivered to the trenched area 67 of the end piece 64 via the tubing 28. The endface 66 provides a much larger area for atomization to take place as compared to that of the normal nozzle tip 22 and enables the single-nozzle device 10 to dramatically increase the throughput of droplet production.

Replacement of the central channel for liquid flow found in the prior art in each individual single-nozzle device 10 by external liquid feed via a tubing 28 to the normal nozzle endface 22 or the enlarged nozzle endface 26, 66 eliminates the additional fabrication steps required in constructing the central channel and will, in turn, significantly lower the ultimate manufacturing costs of single-nozzle devices 10 and nozzle-array devices 50.

Thus, the single-nozzle device 10 and the nozzle-array device 50 are capable of providing all the desirable features enumerated at the outset above, namely, monodisperse or narrowly-sized droplets with optimum size range (1 to 6 μm), high throughput and thus reduced treatment time, small physical size for easy access to target, and very low electrical drive power. These desirable features, together with the aforementioned unique capabilities, should facilitate development of new technologies for systemic therapy via the lung by absorption through alveoli.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for atomizing a liquid into monodisperse or narrowly sized droplets comprising:

issuing the liquid to be atomized from an external conduit onto or adjacent to a nozzle endface disposed at the distal end of at least one ultrasonic single-nozzle device;

driving the at least one ultrasonic single-nozzle device at its resonance frequency;

atomizing the liquid on the nozzle endface of the at least one ultrasonic single-nozzle device; and directing the atomized liquid onto an outside surface, wherein driving the at least one ultrasonic single-nozzle device at its resonance frequency comprises progressively increasing an overall vibration amplitude magnification through a plurality of Fourier horns disposed within the at least one ultrasonic single-nozzle device.

2. The method of claim 1 where atomizing the liquid on the nozzle endface of the at least one ultrasonic single-nozzle device comprises vibrating the nozzle endface in the direction perpendicular or nearly perpendicular to the nozzle endface until at least a critical vibration amplitude threshold is reached for the at least one ultrasonic single-nozzle device.

3. The method of claim 1 where issuing the liquid to be atomized from an external conduit onto a nozzle endface disposed at the distal end of at least one ultrasonic single-nozzle device comprises disposing a plurality of liquids to be atomized on or adjacent to the nozzle endface contemporaneously with ultrasonic energy provided to the nozzle endface by a plurality of ultrasonic single-nozzle devices disposed in parallel within a nozzle-array device.

4. The method of claim 2 where atomizing the liquid on the nozzle endface of the at least one ultrasonic single-nozzle device further comprises forming a layer of the liquid to be atomized across the endface of a nozzle tip of the at least one ultrasonic single-nozzle device.

5. The method of claim 1 where directing the atomized liquid onto an outside surface comprises delivering the atomized liquid for inhalation or pulmonary drug therapy, coating of thin-films, micro-encapsulating of drugs, coating of three dimensional micro- and nano-electronics or photonics, or synthesizing of nano-particles.

6. The method of claim 1 where driving the at least one ultrasonic single-nozzle device at its resonance frequency comprises driving a piezoelectric transducer coupled to the at least one ultrasonic single-nozzle device by means of a function generator and amplifier.

7. The method of claim 3 where driving the at least one ultrasonic single-nozzle device at its resonance frequency comprises coupling the plurality of ultrasonic single-nozzle devices configured in parallel within the nozzle-array device so that a plurality of nodal bars disposed on each of the plurality of ultrasonic single-nozzle devices are in contact mechanically or otherwise coupled.

8. The method of claim 1 where issuing the liquid to be atomized from an external conduit onto or adjacent to a nozzle endface disposed at the distal end of at least one ultrasonic single-nozzle device comprises turning the liquid to be atomized on and off intermittently and delivering a corresponding atomized liquid intermittently.

9. The method of claim 1 producing monodisperse or narrowly-sized droplets using a vibrating solid endface with an excitation amplitude exceeding the required critical vibration amplitude.

* * * * *